United States Patent [19]

Brenner et al.

[11] Patent Number: 5,462,932
[45] Date of Patent: Oct. 31, 1995

[54] ORAL LIQUID ALENDRONATE FORMULATIONS

[75] Inventors: Gerald S. Brenner; Ashok V. Katdare, both of Norristown, Pa.; Denise Pretzer, Chesterfield, Mo.; Donna T. Whiteford, Brooklyn, N.Y.

[73] Assignee: Merck & Co., Inc., Rahway, N.J.

[21] Appl. No.: 245,289

[22] Filed: May 17, 1994

[51] Int. Cl.$^6$ .................. A61K 31/66; A61K 31/685
[52] U.S. Cl. ............................................. 514/108
[58] Field of Search ................................. 514/108

[56] References Cited

U.S. PATENT DOCUMENTS

| | | | |
|---|---|---|---|
| 4,922,007 | 5/1990 | Kieczykowski et al. | 562/13 |
| 5,002,937 | 3/1991 | Bosies | 514/108 |
| 5,019,651 | 5/1991 | Kieczykowski | 562/13 |
| 5,227,506 | 7/1993 | Saari et al. | 514/108 |
| 5,270,365 | 12/1993 | Gertz et al. | 514/108 |
| 5,356,887 | 10/1994 | Brenner et al. | 514/108 |
| 5,376,649 | 12/1994 | Pohjala et al. | 514/108 |

*Primary Examiner*—Richard L. Raymond
*Attorney, Agent, or Firm*—Robert J. North; Joanne M. Giesser; Melvin Winokur

[57] ABSTRACT

Disclosed is a therapy protocol for treating and for preventing bone loss in patients who have difficulty in swallowing by administering a liquid formulation of alendronate which can be easily swallowed. Also described are pharmaceutical dosage forms of a syrup, aqueous solution, a solution formed from a reconstituted powder, of alendronate, for carrying out the therapeutic method.

25 Claims, No Drawings

ORAL LIQUID ALENDRONATE FORMULATIONS

FIELD OF THE INVENTION

The instant invention relates generally to the use of oral liquid formulations of alendronate, i.e., 4-amino-1-hydroxybutylidene- 1,1-bisphosphonic acid monosodium trihydrate, to inhibit bone resorption in human patients who have difficulty in swallowing.

BACKGROUND OF THE INVENTION

Normal bones are living tissues undergoing constant resorption and redeposition of calcium, with the net effect of maintenance of a constant mineral balance. The dual process is commonly called "bone turnover". In normal growing bones, the mineral deposition is in equilibrium with the mineral resorption, whereas in certain pathological conditions, bone resorption exceeds bone deposition, for instance due to malignancy or primary hyperparathyroidism, or in osteoporosis. In other pathological conditions the calcium deposition may take place in undesirable amounts and areas leading to e.g. heterotopic calcification, osteoarthritis, kidney or bladder stones, atherosclerosis, and Paget's disease which is a combination of an abnormal high bone resorption followed by an abnormal calcium deposition.

Alendronate, 4-amino-1-hydroxybutylidene-1,1 -bisphosphonic acid monosodium trihydrate, is an agent for combating bone resorption in bone diseases including osteoporosis and is described as a composition, method of use and synthesis along with other pharmaceutically acceptable salts in U.S. Pat. Nos. 4,922,007 and 5,019,651 (both assigned to Merck).

There are situations where e.g., an aging female patient is undergoing alendronate therapy for osteoporosis (i.e. rarefaction of bone) or is considered to be at risk for developing osteoporosis and at the same time experiences difficulty in swallowing.

However, alendronate currently is administered orally to all patients as a tablet. The availability of only a solid oral dosage form is a disadvantage for some patients who are unable to readily swallow tablets. Furthermore, these patients may comprise a significant percentage of the alendronate patient population, since the drug is also intended for the aging female patient population.

What is desired in these cases is an effective therapy to optimally treat this aging female patient population with an improved oral formulation to overcome the problem of difficulty in swallowing.

SUMMARY OF THE INVENTION

The present invention provides a method for treating and/or preventing bone loss in a subject who has difficulty in swallowing by the administering to said patient a pharmaceutically effective amount of alendronate, in an oral liquid formulation. The liquid formulation can be in the form of a syrup, an aqueous solution or a reconstituted alendronate powder in a water solution and contains a buffer to regulate the pH of the solution and a complexing agent to prevent the formation of insoluble complexes of alendronate.

The oral liquid pharmaceutical composition of this invention contains a pharmaceutically effective amount of alendronate in a liquid pharmaceutically acceptable carder e.g. purified water, and a buffer, e.g. citrate, to maintain the pH at 2–8 and preferably 4–6 and a complexing agent, e.g. citrate or EDTA, to inhibit the precipitation of alendronate in an aqueous medium. Also provided is the aqueous solution above containing a high concentration of sugar providing a syrup, which can also be flavored for marketing desirability.

Also provided is a pharmaceutical composition comprising a powder for reconstitution containing a pharmaceutically effective amount of alendronate in a pharmaceutically acceptable dry excipient also in the presence of a buffer, e.g. citrate, and complexing agent said powder capable of dissolving in water.

DETAILED DESCRIPTION OF THE INVENTION AND PREFERRED EMBODIMENTS

Oral solutions of alendronate, in the form of a syrup, an aqueous solution, or a reconstituted aqueous solution of a powder offer the advantages of ease of administration, increased compliance for patients who have difficulty swallowing solid oral dosage forms. A powder for reconstitution also offers the additional advantage of minimizing storage space in nursing homes, pharmacies, hospitals and warehouses. These formulations have the advantage of permitting dose titration should this be desired.

The method can be used to treat humans, particular females who are post-menopausal with an osteogenically effective amount of alendronate to inhibit bone resorption in need of such treatment. Such need arises locally in cases of bone fracture, non-union, defect, and the like. Such need also arises in cases of systemic bone disease, as in osteoporosis, osteoarthritis, Paget's disease, osteomalacia, multiple myeloma and other forms of cancer, steroid therapy, and age-related loss of bone mass.

The term "inhibition of bone resorption" as used herein, refers to treatment and prevention of bone loss, especially inhibiting the removal of existing bone either from the mineral phase and/or the organic matrix phase, through direct or indirect alteration of osteoclast formation or activity. Thus, the term "inhibitor of bone resorption" as used herein refers to agents that prevent bone loss by the direct or indirect alteration of osteoclast formation or activity and which may increase bone mass in patient treatment populations.

The term "osteogenically effective" as used herein, means that amount which effects the turnover of mature bone. As used herein, an osteogenically effective dose is also "pharmaceutically effective."

The term "treatment" or "treating" as used herein shall mean (1) providing a subject with an amount of alendronate sufficient to act prophylactically to prevent the development of a weakened and/or unhealthy state; and/or (2) providing a subject with a sufficient amount of alendronate so as to alleviate or eliminate a disease state and/or the symptoms of a disease state, and a weakened and/or unhealthy state.

Pharmaceutical formulations of the invention which include alendronate for administration will generally include an osteogenically effective amount of alendronate to promote bone growth, in addition to a pharmaceutically acceptable excipient. The compositions are advantageously prepared together with dry inert carriers for the powder form such as sugars, including sucrose and lactose, starch and derivatives, cellulose and derivatives, gums, fatty acids and their salts.

For liquid formulations, suitable liquid excipients/carriers are purified water and saline solution.

Other suitable excipients and other accessory additives are as follows:

Solvents ethanol
glycerol
propylene glycol

Stabilizers

EDTA (ethylene diamine tetraacetic acid)

Preservatives sodium benzoate
sorbic acid
methyl p-hydroxy benzoate
propyl p-hydroxy benzoate

Buffering Agents citric acid/sodium citrate
potassium hydrogen tartrate
sodium hydrogen tartrate
potassium hydrogen phthalate
sodium hydrogen phthalate
potassium dihydrogen phosphate
disodium hydrogen phosphate

Flavoring Agents saccharin
lactose
sucrose
fructose
sorbitol
aspartame

Viscosity Agents cellulose derivatives including:
hydroxymethyl cellulose
hydroxypropyl cellulose

Coloring Agents

FD&C Blue 2
FD&C Red 33

In addition, the presence of a buffer is necessary to maintain the aqueous pH in the range of 2–8 and preferably 4–6.

The buffer system is generally a mixture of a weak acid and a soluble salt thereof, e.g., sodium citrate/citric acid; or the monocation or dication salt of a dibasic acid, e.g., potassium hydrogen tartrate; sodium hydrogen tartrate, sodium hydrogen phthalate, potassium hydrogen phthalate, potassium dihydrogen phosphate, and disodium hydrogen phosphate.

The amount of buffer system used is dependent on (1) the desired pH; and (2) the amount of alendronate. Generally, an amount of buffer used is 0.5 to 50:1 mole ratio of buffer:alendronate of formulation to maintain a pH in the range of 2 to 9 and generally, 1 to 10 mole ratio of buffer to alendronate present.

One useful buffer is sodium citrate/citric acid in the range of 5 to 50 mg per ml. sodium citrate to 1 to 15 mg per ml. citric acid.

A complexing agent is also present to prevent the precipitation of alendronate through metal complex formation with dissolved metal ions, e.g., Ca, Mg, Fe, Al, Ba, which may leach out of glass containers or rubber stoppers or be present in ordinary tap water. The agent acts as a competitive complexing agent with the alendronate and produces a soluble metal complex whereas alendronate generally forms an insoluble metal complex. Complexing agents include the citrate buffer, which acts as a buffer/complexing agent or EDTA. When EDTA is used, it is used in an amount of 0.005–0.1% by weight of the composition and 0.005–2 parts of EDTA to 1 part by weight alendronate and preferably about 0.01% by weight of the composition. Preferred is where citrate buffer is used alone.

Examples of three oral dosage forms of alendronate are:

Aqueous Oral Solution

Alendronate bulk drug is dissolved in water or appropriate cosolvents to reach the desired concentration. Flavoring agents, coloring agents, viscosity agents, preservatives, stabilizers, and buffering agents are added as required. The solution is filled into multi- or unit-dose packages.

The aqueous solution is used as is directly from the bottle.

| General Formulation | |
|---|---|
| Alendronate | 0.5–10.0 mg |
| Sodium Citrate | 5–50 mg |
| Citric Acid | 1–15 mg |
| Purified Water | q.s. 1 mL |

Additional agents such as cosolvents, flavoring agents, coloring agents, preservatives, stabilizers and buffering agents may also be specifically incorporated in the formulation as follows:

| Specific Formulation | |
|---|---|
| Alendronate | 0.5–10.0 mg |
| Sodium Citrate | 5–50 mg |
| Citric Acid | 1–15 mg |
| Wild Cherry (powder)[a] | 10–200 mg |
| FDC Red No. 33[b] | 0.1–1.0 mg |
| Sorbic Acid | 0.05–0.2% |
| Saccharin[c] | 1–100 mg |
| Propylene Glycol | 5–20% |
| Purified Water | q.s. 1 mL |

[a]Flavorings other than Wild Cherry may also be utilized.
[b]Coloring other than FDC No. 33 may also be chosen to match other flavors.
[c]Sucrose or aspartame may alternatively be used for sweetening.

Oral Syrup

Alendronate bulk drug is incorporated into a solution of sucrose (10–85%) to reach the desired concentration. Additional agents such as glycerin, sorbitol, flavoring agents, coloring agents, viscosity agents, preservatives, stabilizers, and buffering agents are added as required. The final solution is filled into multi- or unit-dose packages.

The syrup can be used as is directly from the bottle or added to a small amount of tap water for ease in swallowing.

| General Formulation | |
|---|---|
| Alendronate | 0.5–10.0 mg |
| Citric Acid | 1–15 mg |

-continued

| General Formulation | |
|---|---|
| Sodium Citrate | 5–50 mg |
| Sucrose | 10–85% |
| Purified Water | q.s. 1 mL |

Additional agents such as glycerin, sorbitol, flavoring agents, coloring agents, preservatives, stabilizers and buffering agents may also be specifically incorporated in the formulation as follows:

| Specific Formulation | |
|---|---|
| Alendronate | 0.5–10.0 mg |
| Citric Acid | 1–15 mg |
| Sodium Citrate | 5–50 mg |
| Glycerin | 5–25% |
| Sucrose | 10–40% |
| Sorbitol | 10–40% |
| Wild Cherry (powder)[a] | 10–200 mg |
| FDC Red No. 33[b] | 0.1–1.0 mg |
| Sorbic Acid | 0.05–0.2% |
| Purified Water | q.s. 1 mL |

[a]Flavorings other than Wild Cherry may also be utilized.
[b]Coloring other than FDC No. 33 may also be chosen to match other flavors.

Powder for Reconstitution

Alendronate bulk drug is blended to homogeneity with one or more of the following: flavoring agents, coloring agents, preservatives, stabilizers and specifically with a buffering agent. The powder blend is then filled into multi-dose containers or unit-dose packets.

The powder can be dissolved in ordinary tap water to reconstitute the alendronate in an aqueous solution.

| Powder Formulation for Reconstitution | |
|---|---|
| | Amount per Unit-Dose Container:[d] |
| Alendronate | 2–50 mg |
| Sucrose | 100–1000 mg |
| Sodium Citrate | 25–500 mg |
| Citric Acid | 5–500 mg |

[d]Container may be a bottle (to which water may be added) or sachet packet. Alteratively, the formulation may be provided as a bulk in a multi-dose container.

The precise dosage necessary will vary with the age, size, sex and condition of the subject, the nature and severity of the disorder to be treated, and the like; thus, a precise effective amount cannot be specified in advance and will be determined by the caregiver. However, appropriate amounts may be determined by routine experimentation with animal models, as described below. In general terms, an effective dose for alendronate in any of the oral liquid formulations is about 1.5 to 3000 µg/kg of body weight and preferably about 10 µg/kg to about 200 µg/kg of body weight.

The methods and compositions of the invention are useful for treating bone fractures, defects and disorders which result from the pathological conditions of osteoporosis, osteoarthritis, Paget's disease, osteohalisteresis, osteomalacia, bone loss resulting from multiple myeloma other forms of cancer, bone loss resulting from side effects of other medical treatment (such as steroids), and age-related loss of bone mass.

What is claimed is:

1. A pharmaceutical composition comprising a pharmaceutically effective amount of alendronate, in a pharmaceutically acceptable carrier and a sufficient amount of a buffer to maintain a pH of the composition in the range of 2 to 8 and complexing agent to prevent the precipitation of alendronate in aqueous solution.

2. The pharmaceutical composition of claim 2 being a liquid.

3. The pharmaceutical composition of claim 3, wherein said liquid is a syrup.

4. The pharmaceutical composition of claim 2, wherein said liquid is an aqueous solution.

5. The pharmaceutical composition of claim 1 being a powder for reconstitution.

6. The pharmaceutical composition of claim 5 dissolved in water.

7. The pharmaceutical composition of claim 1 wherein said alendronate is present in the amount of 0.0005 to 0.5 grams per gram of composition.

8. The pharmaceutical composition of claim 1 wherein said pharmaceutically acceptable excipient is purified water.

9. The pharmaceutical composition of claim 1 wherein said buffer is sodium citrate/citric acid, potassium hydrogen tartrate, sodium hydrogen tartrate, potassium dihydrogen phosphate, and disodium hydrogen phosphate.

10. The pharmaceutical composition of claim 1 wherein said buffer is present in an amount of 0.5 to 50 to 1 mole ratio of buffer:alendronate.

11. The pharmaceutical composition of claim 1 wherein said complexing agent is EDTA.

12. The pharmaceutical composition of claim 11 wherein said EDTA is present at a ratio of 0.005–2:1 parts by weight per part of alendronate by weight.

13. The pharmaceutical composition of claim 1 wherein said pH is in the range of 4–6.

14. The pharmaceutical composition of claim 1 being a syrup of the following formula:

| Alendronate | 0.5–10.0 mg |
|---|---|
| Citric Acid | 1–15 mg |
| Sodium Citrate | 5–50 mg |
| Sucrose | 10–85% |
| Purified Water | q.s. 1 mL |

15. The pharmaceutical composition of claim 14 being a syrup of the following formula:

| Alendronate | 0.5–10.0 mg |
|---|---|
| Citric Acid | 1–15 mg |
| Sodium Citrate | 5–50 mg |
| Glycerin | 5–25% |
| Sucrose | 10–40% |
| Sorbitol | 10–40% |
| Wild Cherry (powder)[a] | 10–200 mg |
| FDC Red No. 33[b] | 0.1–1.0 mg |
| Sorbic Acid | 0.05–0.2% |
| Purified Water | q.s. 1 mL |

16. The pharmaceutical composition of claim 1 being an aqueous solution of the following formula:

| | |
|---|---|
| Alendronate | 0.5–10.0 mg |
| Sodium Citrate | 5–50 mg |
| Citric Acid | 1–15 mg |
| Purified Water | q.s. 1 mL |

17. The pharmaceutical composition of claim 16 having the formula:

| | |
|---|---|
| Alendronate | 0.5–10.0 mg |
| Sodium Citrate | 5–50 mg |
| Citric Acid | 1–15 mg |
| Wild Cherry (powder)[a] | 10–200 mg |
| FDC Red No. 33[b] | 0.1–1.0 mg |
| Sorbic Acid | 0.05–0.2% |
| Saccharin[c] | 1–100 mg |
| Propylene Glycol | 5–20% |
| Purified Water | q.s. 1 mL |

18. The pharmaceutical composition of claim 1 being a powder for reconstitution of the following formula:

| | |
|---|---|
| Alendronate | 2–50 mg |
| Sucrose | 100–1000 mg |
| Sodium Citrate | 25–500 mg |
| Citric Acid | 5–500 mg |

19. A method for treating and/or preventing bone loss in a subject who has difficulty in swallowing, comprising administering a pharmaceutically effective dose of an oral liquid containing the alendronate pharmaceutical composition as defined in claim 1.

20. The method of claim 19, wherein said subject is human.

21. The method of claim 19, wherein the bone loss is osteoporosis-related, due to disuse, age-related, related to steroid therapy, rheumatoid-related, related to Paget's disease, or related to cancer.

22. The method of claim 19, wherein the treatment is prophylactic.

23. The method of claim 19, wherein said liquid is a syrup.

24. The method of claim 19, wherein said liquid is an aqueous solution.

25. The method of claim 19, wherein said liquid is an aqueous solution formed from a powder for reconstitution.

* * * * *